(12) United States Patent
Yim

(10) Patent No.: US 6,886,553 B2
(45) Date of Patent: May 3, 2005

(54) SELF-CONTAINED PERSONAL WARMING APPARATUS AND METHOD OF WARMING

(75) Inventor: Daniel H. Yim, Dalton, GA (US)

(73) Assignee: Heatmax, Inc., Dalton, GA (US)

( * ) Notice: Subject to any disclaimer, the term of this patent is extended or adjusted under 35 U.S.C. 154(b) by 87 days.

(21) Appl. No.: 10/405,668

(22) Filed: Apr. 1, 2003

(65) Prior Publication Data

US 2004/0199231 A1 Oct. 7, 2004

(51) Int. Cl.[7] ................................................. F24J 1/00
(52) U.S. Cl. .................. 126/263.02; 126/204; 607/114
(58) Field of Search ........................ 126/263.01, 263.02, 126/204; 62/4; 607/714, 108–114; 2/158, 160

(56) References Cited

U.S. PATENT DOCUMENTS

| | | | |
|---|---|---|---|
| 1,953,513 A | 4/1934 | Simmons | |
| 2,288,745 A | 7/1942 | Sammis | 128/403 |
| 3,307,554 A | 3/1967 | Thornton et al. | 128/402 |
| 3,585,736 A | 6/1971 | Polichena | 36/2.6 |
| 3,587,578 A | 6/1971 | Walker | 128/268 |
| 3,780,537 A | 12/1973 | Spencer | 62/530 |
| 3,815,610 A | 6/1974 | Winther | 128/380 |
| 3,871,376 A | 3/1975 | Kozak | 128/275.1 |
| 3,889,684 A | 6/1975 | Lebold | 128/402 |
| 3,900,035 A | 8/1975 | Welch et al. | 128/402 |
| 3,951,127 A | 4/1976 | Watson et al. | 128/206 |
| 4,023,282 A | 5/1977 | Ziegelheafer | 36/2.6 |
| 4,033,354 A | 7/1977 | De Rosa | 128/379 |
| 4,049,408 A | 9/1977 | Patel | 62/4 |
| 4,055,188 A | 10/1977 | Pelton | 128/402 |
| 4,077,390 A | 3/1978 | Stanley et al. | 126/263 |
| 4,081,150 A | 3/1978 | Tyson | 128/402 |
| 4,106,478 A | 8/1978 | Higashijima | 126/263 |
| 4,190,054 A | 2/1980 | Brennan | 128/402 |
| 4,249,319 A | 2/1981 | Yoshida | 36/2.6 |
| 4,326,533 A | 4/1982 | Henderson | 128/402 |
| 4,331,731 A | 5/1982 | Seike et al. | 428/305.5 |
| 4,372,318 A | 2/1983 | Viesturs et al. | 128/403 |
| 4,381,025 A | 4/1983 | Schooley | 150/2.4 |
| 4,516,564 A | 5/1985 | Koiso et al. | 126/263 |
| 4,535,482 A | 8/1985 | Spector et al. | 2/160 |
| 4,543,671 A | 10/1985 | Monk | 2/158 |
| RE32,026 E | 11/1985 | Yamashita et al. | 126/263 |
| 4,649,895 A | 3/1987 | Yasuki et al. | 126/263 |
| 4,658,515 A | 4/1987 | Oatman | 36/44 |
| 4,669,476 A | 6/1987 | Gordon et al. | 128/399 |
| 4,676,223 A | 6/1987 | Peterson | 126/208 |
| 4,676,247 A | 6/1987 | Van Cleve | 128/402 |
| 4,686,993 A | 8/1987 | Grumbine | 128/581 |
| 4,756,299 A | 7/1988 | Podella | 126/263 |
| 4,834,654 A | 5/1989 | Nussbaum | 433/141 |
| 4,872,442 A | 10/1989 | Manker | 126/263 |
| 4,880,953 A | 11/1989 | Manker | 219/10.55 |
| 4,925,743 A | 5/1990 | Ikeda et al. | 428/702 |

(Continued)

FOREIGN PATENT DOCUMENTS

JP        57-31980        *    2/1982

Primary Examiner—James C. Yeung
(74) Attorney, Agent, or Firm—Thomas, Kayden, Horstemeyer & Risley, LLP

(57) ABSTRACT

A self-contained disposable single-use heat generating apparatus comprising a heat generating pack having a first bag layer defined by a first surface area bonded to a second bag layer defined by a second surface area and creating a pouch therebetween. A heat generating agent is disposed within the pouch and adapted to consume air at a predetermined consumption rate in an exothermic reaction. At least a portion of one of the first surface area and the second surface area comprises an air permeable surface area having a predetermined airflow rate such that the heat generating agent remains substantially evenly distributed within the pouch. A method of providing therapeutic heat is also provided.

11 Claims, 2 Drawing Sheets

U.S. PATENT DOCUMENTS

| | | | |
|---|---|---|---|
| 4,934,336 A | 6/1990 | White | 126/263 |
| 4,948,951 A | 8/1990 | Balzano | 219/528 |
| 4,981,135 A | 1/1991 | Hardy | 128/402 |
| 5,008,517 A | 4/1991 | Brekkestran et al. | 219/211 |
| 5,020,509 A | 6/1991 | Suzuki et al. | 126/263 |
| 5,020,711 A | 6/1991 | Kelley | 224/222 |
| 5,032,705 A | 7/1991 | Batcheller et al. | 219/211 |
| 5,035,003 A | 7/1991 | Rinehart | 2/159 |
| 5,046,479 A | 9/1991 | Usui | 126/204 |
| 5,058,563 A | 10/1991 | Manker | 126/263 |
| 5,084,986 A | 2/1992 | Usui | 36/2.6 |
| 5,187,814 A | 2/1993 | Gold | 2/160 |
| 5,205,278 A | 4/1993 | Wang | 126/263 |
| 5,230,170 A | 7/1993 | Dahle | 36/26 |
| 5,230,333 A | 7/1993 | Yates et al. | 128/382 |
| 5,233,981 A | 8/1993 | Miyashita | 607/114 |
| 5,304,216 A | 4/1994 | Wallace | 607/112 |
| 5,310,400 A | 5/1994 | Rogers et al. | 602/5 |
| 5,324,318 A | 6/1994 | Smith | 607/104 |
| 5,339,796 A | 8/1994 | Manker | 126/263 |
| 5,342,412 A | 8/1994 | Ueki | 607/114 |
| 5,366,492 A | 11/1994 | Ueki | 607/114 |
| 5,378,531 A | 1/1995 | Larson et al. | 428/255 |
| 5,409,500 A | 4/1995 | Dyrek | 607/111 |
| 5,425,975 A * | 6/1995 | Koiso et al. | 428/74 |
| 5,477,847 A | 12/1995 | Ueki | 126/263.07 |
| 5,509,143 A | 4/1996 | Yates et al. | 2/160 |
| 5,531,775 A | 7/1996 | Sasaki et al. | 607/96 |
| 5,541,388 A | 7/1996 | Gadd | 219/211 |
| 5,571,155 A | 11/1996 | Bastille | 607/114 |
| 5,572,744 A | 11/1996 | Reid, Jr. et al. | 2/158 |
| 5,617,583 A | 4/1997 | Yates et al. | 2/160 |
| RE35,586 E | 8/1997 | Manker | 126/263.03 |
| 5,674,270 A | 10/1997 | Viltro et al. | 607/112 |
| 5,676,642 A | 10/1997 | Peters | 602/27 |
| 5,697,962 A | 12/1997 | Brink et al. | 607/108 |
| 5,718,955 A | 2/1998 | McGuire et al. | 428/35.7 |
| 5,766,235 A | 6/1998 | Kostopoulos | 607/114 |
| 5,774,894 A | 7/1998 | Yates et al. | 2/158 |
| 5,777,296 A | 7/1998 | Bell | 219/211 |
| 5,800,492 A | 9/1998 | Manker | 607/111 |
| 5,837,005 A | 11/1998 | Viltro et al. | 607/112 |
| 5,879,378 A | 3/1999 | Usui | 607/96 |
| 5,885,597 A | 3/1999 | Botknecht et al. | 424/401 |
| 5,887,437 A | 3/1999 | Maxim | 62/4 |
| 5,891,187 A | 4/1999 | Winthrop et al. | 607/96 |
| 5,918,590 A * | 7/1999 | Burkett et al. | 126/263.02 |
| 5,928,275 A | 7/1999 | Yates et al. | 607/112 |
| 5,968,072 A | 10/1999 | Hite et al. | 606/202 |
| 6,055,670 A | 5/2000 | Parker | 2/161.1 |
| 6,060,693 A | 5/2000 | Brown | 219/211 |
| 6,141,801 A | 11/2000 | Helenick | 2/159 |
| 6,218,644 B1 | 4/2001 | Zorn et al. | 219/211 |
| 6,239,410 B1 | 5/2001 | Tackore | 219/211 |
| 2003/0055366 A1 | 3/2003 | Chalek | 602/2 |

* cited by examiner

SELF-CONTAINED PERSONAL WARMING APPARATUS AND METHOD OF WARMING

TECHNICAL FIELD

The present invention is generally related to warming devices and, more particularly, is related to a self-contained personal warming apparatus and method of warming.

BACKGROUND OF THE INVENTION

Heat generating pouches of various configurations and shapes are designed and used for various purposes, such as hand warming, feet warming, and the like, by placing the heat generating pouch in a glove, mitten, shoe, etc. Heat generating pouches typically comprise a heat generating compound disposed between at least two layers of material, such as fabric, or the like, assembled to form a pouch. The heat generating compound emits heat during an exothermic chemical reaction resulting from exposure of the compound to air. Known heat generating compounds typically comprises a loose granular substance that is freely movable within the pouch. With a freely movable compound, when the pouch is placed flat, or horizontally, the compound is somewhat evenly distributed throughout the pouch. However, when the pouch is placed vertically, moved around, or jostled, the compound is drawn by gravity, shifts and settles toward one end of the pouch. This shifting and settling of the compound is sometimes referred to as a "tea-bag" effect. The tea-bag effect results in an uneven temperature profile along the surface area of the pouch. An uneven temperature profile can result in some areas not receiving heat, as desired, or an over concentration of heat in other areas.

The problem of the compound tending to shift and settle within the pouch has been addressed by other configurations of heat generating pouches. In one embodiment, the heat generating compound is contained within pucks or pellets that are disposed between at least two layers of material. The pucks or pellets comprise a heat generating compound capable of reacting with air in an exothermic reaction. The compound is compressed into concentrated, substantially rigid, pellets. In this configuration, however, the heat emission is concentrated at the pucks, resulting in an uneven heat distribution across the surface area of the pouch. Furthermore, because the pucks are rigid, the pucks do not conform to various contours of the human body against which the heat generating pouch may be placed.

The undesirable effect of a shifting compound has also been addressed by introducing air to the heat generating compound through only one of the two layers of material forming the pouch, while the other of the two layers of material comprises a self-adhesive. However, these adhesive pouches can not be easily inserted into pockets formed in socks, gloves, mittens, specially designed belts, or the like for use. Indeed, such adhesive pouches are typically fixed to an interior surface of a user's clothing. In this configuration of use, the pouch moves away from the user's skin as the clothing moves away from the user's skin. Furthermore, fixing the pouch to a user's clothing typically results in minimal or no pressure being applied to the pouch as the pouch is applied to the user's skin, thereby rendering the pouch less effective.

Thus, a heretofore unaddressed need exists in the industry to address the aforementioned deficiencies and inadequacies.

SUMMARY OF THE INVENTION

Preferred embodiments of the present invention provide a self-contained disposable single-use heat generating apparatus and method of use. Briefly described, in architecture, one embodiment of the apparatus can be implemented as follows. A self-contained disposable single-use heat generating apparatus comprises a heat generating pack having a first bag layer bonded to a second bag layer creating a pouch therebetween. A heat generating agent is disposed in the pouch. At least a portion of one of the first bag layer and the second bag layer has an air permeable surface area with a predetermined airflow rate. The airflow rate through the air permeable surface area is predetermined such that the heat generating agent remains substantially evenly distributed within the pouch.

Preferred embodiments of the present invention can also be viewed as a method for providing therapeutic heat. In this regard, one embodiment of such a method, among others, can be broadly summarized by the following steps: containing a heat generating composition in a self-contained heat generating pack and introducing air to the heat generating composition such that the heat generating composition remains substantially evenly distributed within the heat generating pack.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1:
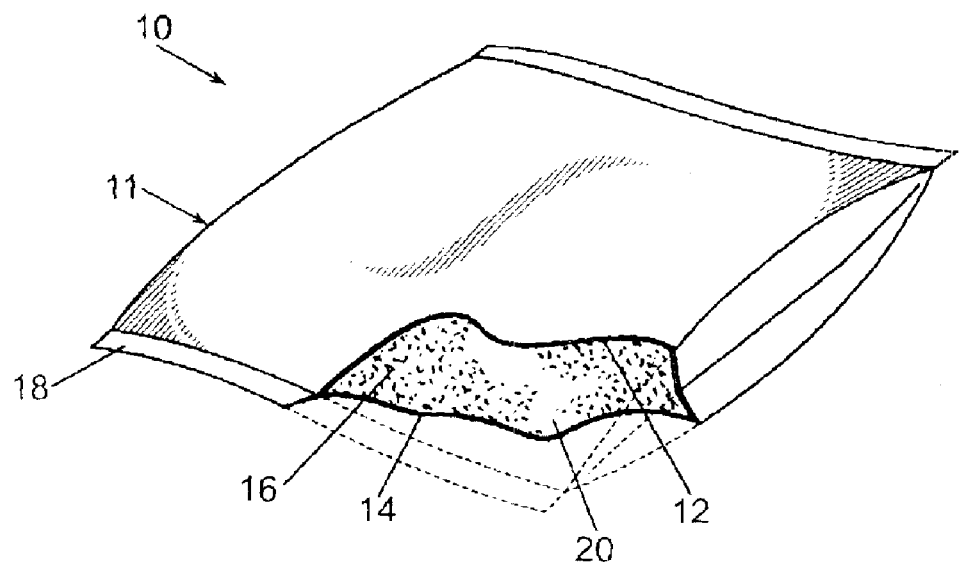
FIG. 1 is a cutaway perspective view of an embodiment of the self-contained personal warming apparatus of the present invention.

FIG. 1 illustrates one preferred embodiment of a self-contained disposable single-use heat generating apparatus 10 of the present invention. A heat generating pack 11 comprises a first bag layer 12, a second bag layer 14 and a heat generating agent 16 disposed therebetween. The first bag layer 12 is defined by a first set of dimensions and has a first surface area. The second bag layer 14 is defined by a second set of dimensions and has a second surface area. It should be noted that although the dimensions of the first bag layer 12 and the second bag layer 14 are illustrated as being substantially rectangular in shape, the dimensions can form any suitable shape. It is preferred, though not required, that the first surface area substantially corresponds to the second surface area.

The first bag layer 12 and the second bag layer 14 are aligned, one on top of the other, and are fixed together at a seam 18. The seam 18 can either extend around the perimeter of the heat generating pack 11 where the first bag layer 12 and second bag layer 14 meet, or run along one or a plurality of edges thereof. As illustrated in FIG. 1 the seam 18 runs along two opposing edges. The seam 18 is created in any suitable manner, for example by melting or bonding.

An enclosed space, or pouch 20, is created between the first bag layer 12 and the second bag layer 14. At least a portion of one of the first surface area and/or the second surface area are preferably air permeable as discussed in greater detail below. The first bag layer 12 and the second bag layer 14 preferably comprise a flexible fabric, material, or the like.

A heat generating agent 16 is disposed within the pouch 20 and contained therein. The heat generating agent 16 comprises a main ingredient of iron powder and incorporates therein, water, a water retaining material (charcoal, vermiculite, or the like), an oxidation promoter, such as activated carbon, and salt. More particularly, and as an example, the agent 16 may comprise approximately 35–50% by weight of iron powder, 25–45% by weight of water, approximately 10–14% by weight of water retaining agent, and approximately 4.5–6% by weight of salt. Upon exposure to air, oxidation of the iron begins in an exothermic reaction. The heat generated by the exothermic reaction of the agent 16 passes through the first bag layer 12 and the second bag layer 14 and radiates from the apparatus 10. It is preferable that the heat radiating from the apparatus 10 ranges from 39–45° C. in order to provide a level of heat suitable for therapeutic heating without danger of burn to human skin.

During the exothermic reaction, the heat generating agent 16 consumes air at a predetermined air consumption rate. Controlling the rate of introduction of air to the heat generating agent 16 effects both the temperature radiated from the pack 11 as well as the shifting of the agent 16 within the pouch 20. Generally, the more air introduced to the heat generating agent 16, the hotter the pack 11 will become. Also, where the heat generating agent 16 consumes air faster than air is introduced to thereto, a vacuum will be created.

Figure 1A:
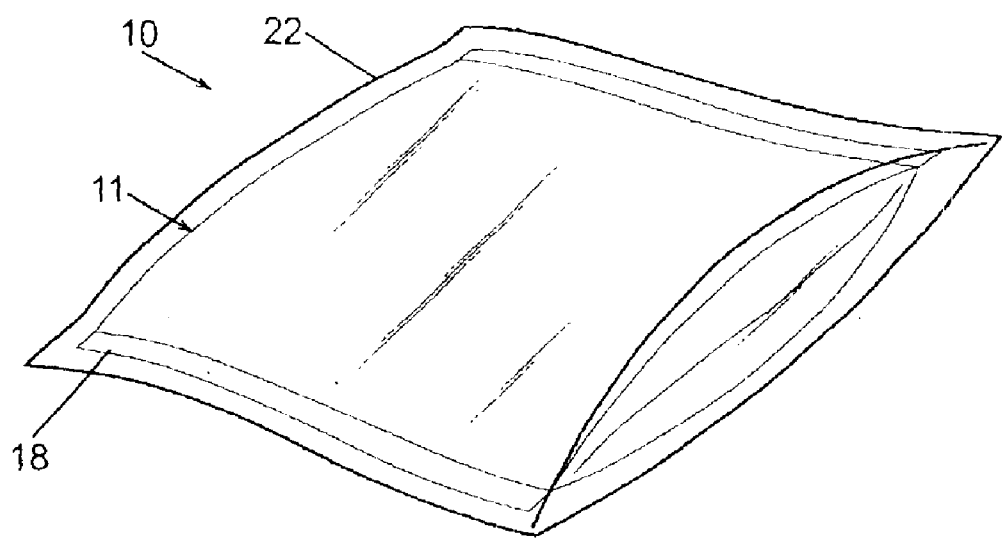
FIG. 1A is a perspective view of an embodiment of a self-contained personal warming apparatus illustrated in FIG. 1.

More specifically, and with reference to FIG. 1A, an embodiment of the self-contained disposable single-use heat generating apparatus 10 is illustrated. In this embodiment, the heat generating pack 11 is disposed inside a protective package 22. The protective package 22 can be hermetically sealed with the heat generating pack 11 inside such that no air or minimal air is introduced to the heat generating pack 11. In this embodiment, the protective package 22 effectively eliminates the introduction of air to the agent 16 thereby substantially preventing the heat generating exothermic reaction. The heat generating pack 11 is disposed within the protective package 22 preferably at, or closely after, the time of manufacture, and the heat generating apparatus 10 can be marketed, sold and stored in this configuration.

Figure 2:
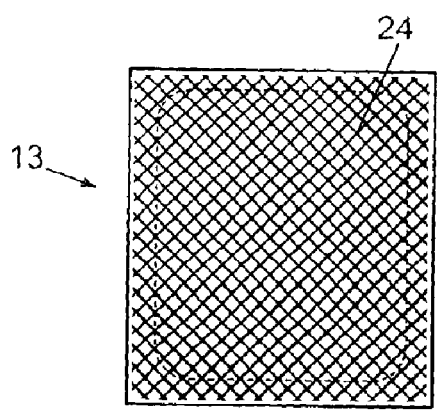
FIG. 2 is a plan view of an embodiment of a bag layer of the apparatus illustrated in FIG. 1.
Figure 3:
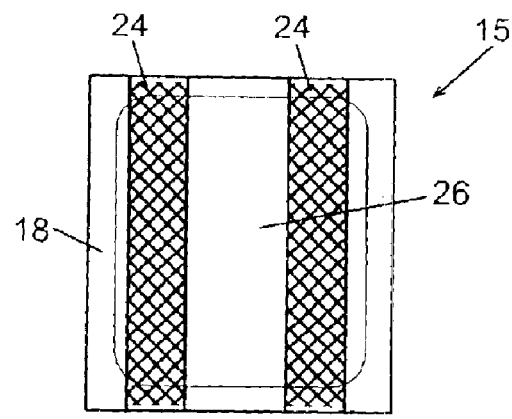
FIG. 3 is a plan view of an embodiment of a bag layer of the apparatus illustrated in FIG. 1.
Figure 4:
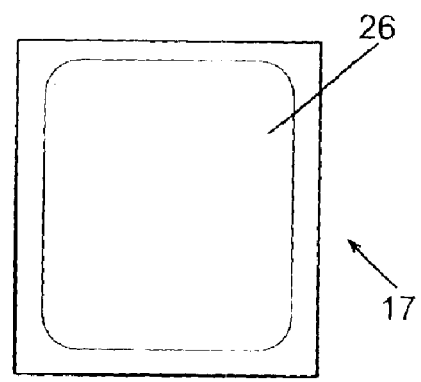
FIG. 4 is a plan view of an embodiment of a bag layer of the apparatus illustrated in FIG. 1.

Referring next to FIGS. 2–4, various embodiments of bag layers 13, 15 and 17 are illustrated. The bag layers 13, 15 and 17 can comprise the first bag layer 12, the second bag layer 14 or any suitable combination thereof in order to form a heat generating pack 11. For example, a heat generating pack 11 can comprise a first bag layer 12 arranged in the configuration of bag layer 13 (FIG. 2) and a second bag layer 14 arranged in the configuration of bag layer 17 (FIG. 4).

Selection of the configuration of first bag layer 12 and second bag layer 14 is driven by a desired airflow rate for introduction of air to the heat generating agent 16. An air consumption rate of the heat generating agent 16 being at least slightly greater than an airflow introduction rate to the agent 16 generates at least a slight vacuum inside the pouch 20. The vacuum created inside the pouch 20 reduces shifting and settling of the heat generating agent 16, or "teabagging," within the pouch 20.

The substantially stationary disposition of the heat generating agent 16 inside the pouch 20 results in a heat generating pack 11 that maintains a substantially constant thickness. A substantially even heat profile is emitted across the surface area of the first bag layer 12 and the second bag layer 14. The airflow rate through the combined first surface area and second surface area of the first bag layer 12 and second bag layer 14 preferably is less than the predetermined air consumption rate of the heat generating agent 16 during exothermic reaction. For example, a heat generating pack 11 having porosity allowing an airflow rate of 20,000 sec./100 cc of air preferably contains a heat generating agent 16 having an air consumption rate greater than 20,000 sec./100 cc of air during the exothermic reaction.

Referring more specifically to FIG. 2, one bag layer 13 configuration comprises an air permeable surface area 24. The air permeable surface area 24 preferably comprises a microporous fabric. A preferred microporous fabric can comprise a nonwoven fabric formed from individual fibers that are pressed together forming an interlocking web of fibers. The fibers can be fixed to each other either mechanically (for example, by tangling the fibers together) or chemically (for example, by gluing, bonding, or melting the fibers together). The present invention can comprise a microporous fabric known to one having ordinary skill in the art.

FIG. 3 illustrates a bag layer 15 configuration having a portion of the surface area thereof comprising an air permeable surface area 24 and a portion of the surface area comprising a air impermeable surface area 26. The air permeable surface area 24 preferably comprises a microporous fabric. A preferred microporous fabric for this configuration can comprise a nonwoven fabric formed from individual fibers that are pressed together forming an interlocking web of fibers. The fibers can be fixed to each other either mechanically (for example, by tangling the fibers together) or chemically (for example, by gluing, bonding, or melting the fibers together). This configuration can comprise a microporous fabric known to one having ordinary skill in the art. The air impermeable surface area 26 of the bag layer 15 can comprise polyethelene, polypropylene, or any suitable material. It is preferable that the air impermeable surface area 26 exhibits a low coefficient of friction, such as to allow the heat generating pack 11 to easily slide into a pocket (not shown) formed in a glove, sock, belt for holding heat generating packs in position, or the like. The preferred combination of air permeable surface area 24 and air impermeable surface area 26 of the bag layer 15 of FIG. 3 is determined by the desired air flow introduction rate to the heat generating agent 16 inside a pouch 11 this bag layer 15 configuration may be used to form.

FIG. 4 illustrates another bag layer 17 configuration. The bag layer 17 comprises an air impermeable surface area 26, such as polyethelene, or any suitable material. It is preferable that the air impermeable surface area 26 exhibits a low coefficient of friction, such as to allow the heat generating pack 11 to easily slide into a pocket (not shown) formed in a glove, sock, belt for holding heat generating packs in position, or the like.

Applying the above disclosed bag layer configurations 13, 15 and 17, heat generating packs 11 of various configurations can be formed. One configuration of a heat generating pack 11 comprises a first bag layer 12 comprising bag layer 13 configuration having an air permeable surface area 24 (illustrated in FIG. 2) and a second bag layer 14 comprising bag layer 17 having an air impermeable surface area 26 (illustrated in FIG. 4). In this configuration the rate at which air is introduced to the heat generating agent 16 is controlled by allowing a pre-determined flow rate through the first bag layer 12 and allowing substantially no air flow through the second bag layer 14.

Another configuration of a heat generating pack 11 comprises a first bag layer 12 comprising bag layer 13 having an air permeable surface area 24 (illustrated in FIG. 2) and a second bag layer 14 also comprising bag layer 13 also having an air permeable surface area 24 (illustrated in FIG. 2). In this configuration the rate at which air is introduced to the heat generating agent 16 is controlled by allowing a pre-determined flow rate through both the first bag layer 12 and the second bag layer 14.

A heat generating pack 11 of the present invention can also comprise a first bag layer 12 comprising bag layer 13 having an air permeable surface area 24 (illustrated in FIG. 2) and a second bag layer 14 comprising bag layer 15 having a portion of the surface area being air permeable 24 and a portion of the surface area being air impermeable 26 (illustrated in FIG. 3). In this configuration the rate at which air is introduced to the heat generating agent 16 is controlled by the total air permeable surface area 24 of the first bag layer 12 and the second bag layer 14 combined. It is preferable that the airflow rate through the total air permeable surface area 24 of the first bag layer 12 and the second bag layer 14 combined is less than the air consumption rate of the heat generating agent 16 during exothermic reaction.

A heat generating pack 11 of the present invention can also comprise a first bag layer 12 comprising bag layer 17 having an air impermeable surface area 26 (illustrated in FIG. 4) and a second bag layer 14 comprising bag layer 15 having a portion of the surface area being air permeable 24 and a portion of the surface area being air impermeable 26 (illustrated in FIG. 3). In this configuration the rate at which air is introduced to the heat generating agent 16 is controlled by the total air permeable surface area 24 of the second bag layer 14. It is preferable that the airflow rate through the total air permeable surface area 24 of the second bag layer 14 combined is less than the air consumption rate of the heat generating agent 16 during exothermic reaction.

It should be noted that the above described heat generating packs 11 are mere examples and that any configuration combining air permeable surface area 24 with air impermeable surface area 26 is within the spirit of the present invention.

In one method of use of an embodiment of a self-contained disposable single-use heat generating apparatus 10 of the present invention, a heat generating pack 11 is disposed in a protective package 22 to eliminate, or at least minimize, introduction of air to the heat generating agent 16 disposed inside the pack 11. The heat generating pack 11 is removed from the protective package 22. Air is introduced to a heat generating agent 16 disposed within a pouch 20 of the heat generating pack 11. The pouch 20 is formed by a first bag layer 12 and a second bag layer 14 being peripherally bonded to each other. The heat generating pack 11 is agitated, such as by shaking or crumpling the pack 11 in order to begin or speed up an exothermic reaction of the heat generating agent 16 with air. The heat generating agent 16 consumes air in a heat generating exothermic reaction, thereby emitting heat from the heat generating pack 11. At least one of the first bag layer 12 and the second bag layer 14, or a combination thereof, allow air to be introduced to the heat generating agent 16. The introduction of air is preferably at a flow rate less than the air consumption rate of the heat generating agent 16 during the exothermic reaction. The heat generating pack 11 can be positioned, as desired.

In one method of use, the heat generating pack 11 can be inserted into a pocket, for example a pocket disposed in a belt for heat application near a user's skin on their back, stomach, or any desired location. The heat generating pack 11 can also be inserted into a pocket formed in a sock or glove for a user to warm toes and fingers, respectively.

The exothermic reaction of the heat generating agent 16 when introduced to air produces a heat emission ranging between 39–45° C. for approximately 12 to 18 hours. Upon the conclusion of the exothermic reaction and the cooling down of the heat generating pack 11, the heat generating pack 11 can be removed from the position at which it was placed for use and disposed.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

Therefore, having thus described the invention, at least the following is claimed:

1. A self-contained, disposable, single-use heat generating apparatus, comprising:
   a heat generating pack comprising:
      a first bag layer having a first surface area;
      a second bag layer having a second surface area, said second bag layer being fixed to said first bag layer, such that said first bag layer and said second bag layer defining a pouch therebetween;
      a heat generating agent disposed in said pouch, said heat generating agent arranged and configured to consume air at a predetermined air consumption rate in an exothermic reaction; and
   at least one of said first surface area and said second surface area comprises an air permeable surface area having a predetermined airflow rate at which air is introduced to said heat generating agent, said predetermined airflow rate being arranged and configured to be less than said predetermined air consumption rate such that said heat generating agent remains substantially evenly distributed within said pouch.

2. The apparatus of claim 1, wherein said first bag layer is defined by a set of dimensions substantially corresponding to a set of dimensions defining said second bag layer.

3. The apparatus of claim 1, wherein at least one of said first bag layer and said second bag layer comprises a microporous material.

4. The apparatus of claim 3, wherein said microporous material comprises a fabric having a plurality of fibers forming an inter-locking web, wherein at least a portion of said plurality of fibers are bonded to each other.

5. The apparatus of claim 1, wherein one of said first surface area and said second surface area comprises an air permeable surface area and the other of said first surface area and said second surface area comprises an air permeable surface area.

6. The apparatus of claim 1, wherein one of said first surface area and said second surface area comprises an air permeable surface area and the other of said first surface area and said second surface area comprises an air impermeable surface area.

7. The apparatus of claim 6, wherein said air impermeable surface area comprises a low coefficient of friction.

8. The apparatus of claim 1, further comprising:

a protective package for receiving said heat generating pack, said protective package being air impermeable and retarding said exothermic reaction.

9. The apparatus of claim 8, wherein said protective package is hermetically sealed with said heat generating pack disposed therein.

10. A method for providing therapeutic heat comprising:

containing a heat generating composition having a predetermined air consumption rate in a self-contained heat generating pack;

introducing air to said heat generating composition at a predetermined airflow rate arranged and configured to be less than said air consumption rate such that said heat generating composition remains substantially evenly distributed within said heat generating pack; and providing a low coefficient of friction.

11. The method of claim 10, further comprising:

removing said self-contained heat generating pack from an air impermeable protective package.

* * * * *

(12) EX PARTE REEXAMINATION CERTIFICATE (9174th)
United States Patent
Yim

(10) Number: US 6,886,553 C1
(45) Certificate Issued: Aug. 7, 2012

(54) SELF-CONTAINED PERSONAL WARMING APPARATUS AND METHOD OF WARMING

(75) Inventor: Daniel H. Yim, Dalton, GA (US)

(73) Assignee: Heatmax, Inc., Dalton, GA (US)

Reexamination Request:
No. 90/008,869, Oct. 5, 2007

Reexamination Certificate for:
Patent No.: 6,886,553
Issued: May 3, 2005
Appl. No.: 10/405,668
Filed: Apr. 1, 2003

(51) Int. Cl.
*F24J 1/00* (2006.01)
*F24J 3/00* (2006.01)
*A61F 7/00* (2006.01)

(52) U.S. Cl. .................. 126/263.02; 126/204; 607/114
(58) Field of Classification Search .................. None
See application file for complete search history.

(56) References Cited

To view the complete listing of prior art documents cited during the proceeding for Reexamination Control Number 90/008,869, please refer to the USPTO's public Patent Application Information Retrieval (PAIR) system under the Display References tab.

*Primary Examiner* — Catherine S. Williams

(57) ABSTRACT

A self-contained disposable single-use heat generating apparatus comprising a heat generating pack having a first bag layer defined by a first surface area bonded to a second bag layer defined by a second surface area and creating a pouch therebetween. A heat generating agent is disposed within the pouch and adapted to consume air at a predetermined consumption rate in an exothermic reaction. At least a portion of one of the first surface area and the second surface area comprises an air permeable surface area having a predetermined airflow rate such that the heat generating agent remains substantially evenly distributed within the pouch. A method of providing therapeutic heat is also provided.

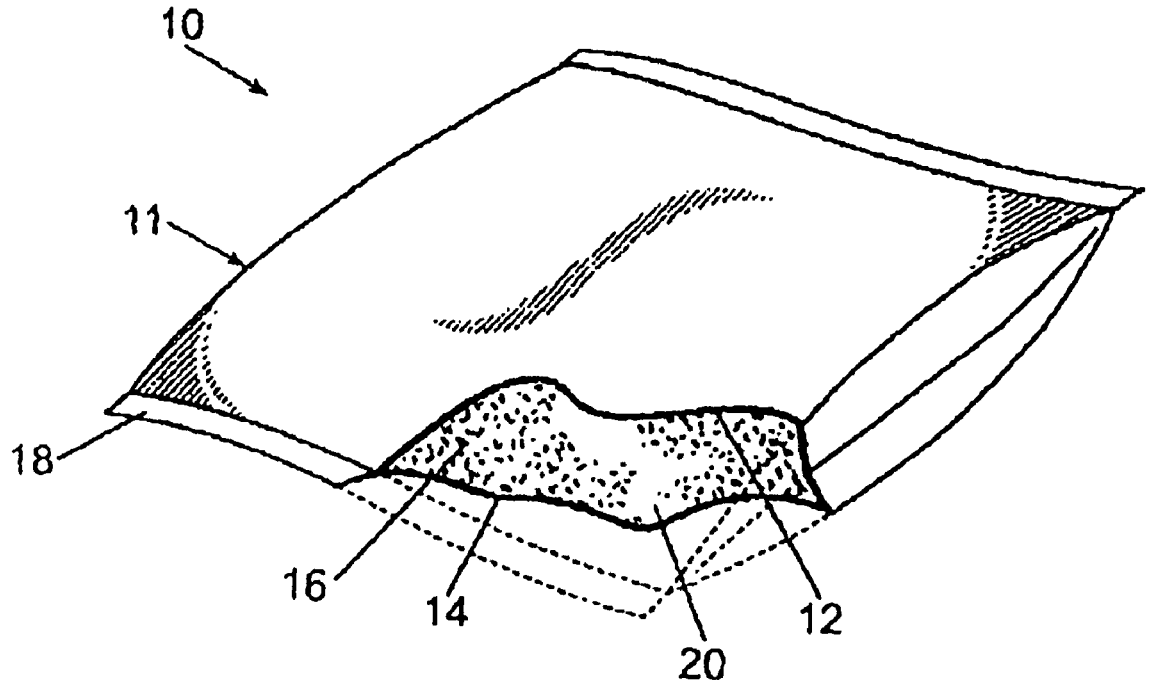

US 6,886,553 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, lines 33-57:

FIG. 3 illustrates a bag layer 15 configuration having a portion of the surface area thereof comprising an air permeable surface area 24 and a portion of the surface area comprising [a] *an* air impermeable surface area 26. The air permeable surface area 24 preferably comprises a microporous fabric. A preferred microporous fabric for this configuration can comprise a nonwoven fabric formed from individual fibers that are pressed together forming an interlocking web of fibers. The fibers can be fixed to each other either mechanically (for example, by tangling the fibers together) or chemically (for example, by gluing, bonding, or melting the fibers together). This configuration can comprise a microporous fabric known to one having ordinary skill in the art. The air impermeable surface area 26 of the bag layer 15 can comprise [polyethelene] *polyethylene*, polypropylene, or any suitable material. It is preferable that the air impermeable surface area 26 exhibits a low coefficient of friction, such as to allow the heat generating pack 11 to easily slide into a pocket (not shown) formed in a glove, sock, belt for holding heat generating packs in position, or the like. The preferred combination of air permeable surface area 24 and air impermeable surface area 26 of the bag layer 15 of FIG. 3 is determined by the desired air flow introduction rate to the heat generating agent 16 inside a pouch 11 this bag layer 15 configuration may be used to form.

Column 4, lines 56-65:

FIG. 4 illustrates another bag layer 17 configuration. The bag layer 17 comprises an air impermeable surface area 26, such as [polyethelene] *polyethylene*, or any suitable material. It is preferable that the air impermeable surface area 26 exhibits a low coefficient of friction, such as to allow the heat generating pack 11 to easily slide into a pocket (not shown) formed in a glove, sock, belt for holding heat generating packs in position, or the like.

AS A RESULT OF REEXAMINATION, IT HAS BEEN DETERMINED THAT:

Claims 1-11 are cancelled.

New claim 12 is added and determined to be patentable.

*12. A self-contained, disposable, single-use heat generating apparatus comprising:*

*a heat generating pack comprising:*

*a first bag layer having a first surface area;*

*a second bag layer having a second surface area, said second bag layer being fixed to said first bag layer, such that said first bag layer and said second bag layer define a pouch therebetween;*

*a heat generating agent disposed in said pouch, said heat generating agent arranged and configured to consume air at a predetermined air consumption rate in an exothermic reaction; and*

*at least one of said first surface area and said second surface area comprises an air permeable surface area having a predetermined airflow rate at which air is introduced to said heat generating agent, said predetermined airflow rate being arranged and configured to be less than said predetermined air comsumption rate such that said heat generating agent remains substantially evenly distributed within said pouch, wherein one of said first surface area and said second surface area comprises an air permeable surface area and the other of said first surface area and said second surface area comprises an air impermeable surface area, wherein said air impermeable surface area comprises a low coefficient of friction; and*

*wherein the air consumption rate exceeds 20,000 sec/100 cc of air.*

* * * * *